(12) United States Patent
Chou et al.

(10) Patent No.: US 6,905,896 B2
(45) Date of Patent: Jun. 14, 2005

(54) SNO₂ ISFET DEVICE, MANUFACTURING METHOD, AND METHODS AND APPARATUS FOR USE THEREOF

(75) Inventors: Jung-Chuan Chou, Yunlin Hsien (TW); Yii Fang Wang, Changhua (TW)

(73) Assignee: National Yunlin University of Science and Technology, Yunlin (TW)

( * ) Notice: Subject to any disclaimer, the term of this patent is extended or adjusted under 35 U.S.C. 154(b) by 0 days.

(21) Appl. No.: 10/419,937

(22) Filed: Apr. 22, 2003

(65) Prior Publication Data

US 2003/0218194 A1 Nov. 27, 2003

(30) Foreign Application Priority Data

May 20, 2002 (TW) ........................................ 91110545 A

(51) Int. Cl.⁷ ........................ G01R 31/26; G01N 27/416
(52) U.S. Cl. ........................ 438/18; 438/49; 324/438; 324/760
(58) Field of Search ............................ 438/14, 48, 49; 324/71.5, 438, 760

(56) References Cited

U.S. PATENT DOCUMENTS

| | | | | |
|---|---|---|---|---|
| 4,397,888 A | * | 8/1983 | Yannopoulos et al. ........ 438/49 |
| 4,641,249 A | * | 2/1987 | Gion et al. ................... 702/25 |
| 5,078,855 A | * | 1/1992 | Mochizuki et al. ......... 204/418 |
| 5,911,873 A | * | 6/1999 | McCarron et al. .......... 205/789 |
| 6,387,724 B1 | * | 5/2002 | Walker ........................ 438/49 |
| 6,531,858 B2 | * | 3/2003 | Chou et al. ................. 324/71.1 |

* cited by examiner

*Primary Examiner*—Amir Zarabian
*Assistant Examiner*—Pamela E Perkins
(74) *Attorney, Agent, or Firm*—Birch, Stewart, Kolasch & Birch, LLP

(57) ABSTRACT

A SnO₂ ISFET device and manufacturing method thereof. The present invention prepares SnO₂ as the detection membrane of an ISFET by sol-gel technology to obtain a SnO₂ ISFET. The present invention also measures the current-voltage curve for different pH and temperatures by a current measuring system. The temperature parameter of the SnO₂ ISFET is calculated according to the relationship between the current-voltage curve and temperature. In addition, the drift rate of the SnO₂ ISFET for different pH and hysteresis width of the SnO₂ ISFET for different pH loop are calculated by a constant voltage/current circuit and a voltage-time recorder to measure the gate voltage of the SnO₂ ISFET.

17 Claims, 7 Drawing Sheets

US 6,905,896 B2

SNO₂ ISFET DEVICE, MANUFACTURING METHOD, AND METHODS AND APPARATUS FOR USE THEREOF

This nonprovisional application claims priority under 35 U.S.C. §119(a) on Patent Application No. 091110545 filed in TAIWAN, R.O.C. on May 20, 2002, which is herein incorporated by reference.

BACKGROUND OF THE INVENTION

1. Field of the Invention

The present invention relates to an ISFET, and in particular to a SnO₂ ISFET device, manufacturing method, and method and apparatus to measure hysteresis width and drift rate therewith.

2. Description of the Related Art

ISFETs (Ion Sensitive Field Effect Transistor) are constructed by substituting a detecting film for the metal gate on the gate oxide of a traditional MOSFET (Metal-Oxide-Semiconductor Field Effect Transistor). When the ISFET is dipped into a solution, the interfacial potential between the detecting film and the solution influences the semiconductor surface since only an extremely thin dielectric (that is, the gate oxide) separates the detecting film from the semiconductor surface. This influences the charge density in the inversion layer of the semiconductor surface, and thereby modulates the channel current through the ISFET. Thus, by utilizing this characteristic, the pH or other ion concentration in a solution can be obtained from the measurement of source/drain current and the gate voltage of the ISFET. The potential difference on the interface between the detecting film and the solution is related to the ion activity in a solution. The hydrogen ion activity in the solution can be measured using different channel currents caused by different interfacial potential differences in various solutions with different hydrogen ion activity.

Patents related to the formation of the ISFET or measurement thereof are listed hereinafter.

U.S. Pat. No. 5,350,701 discloses a method of measuring the content of alkaline-group metals, especially the content of the calcium ions, utilizing chemosynthesis phosphide group as the detecting film on a gate of an ISFET.

U.S. Pat. No. 5,387,328 discloses a bio-sensor using ion sensitive field effect transistor with platinum, wherein an enzyme membrane is immobilized on the ion-detecting film to determine the concentration of glucose.

U.S. Pat. No. 5,414,284 discloses a method of fabricating an ISFET and an ESD protective circuit on the same silicon substrate, wherein a capacitor is utilized as an interface between the protective circuit and a sample solution to the DC leakage current.

U.S. Pat. No. 5,309,085 integrates the measurement circuit of a creature sensor having ISFET on a wafer. The measured circuit has two ISFET devices, an enzyme ISFET and a reference electrode FET, whose output signal can be amplified by a differential amplifier.

U.S. Pat. No. 5,061,976 discloses a carbon thin film on the gate oxide of the ISFET and then a 2,6 xylenol electrolytic polymerization film formed thereon. The ISFET has the ability to detect hydrogen ions and the advantages of small floating time, high reliability, and insensitivity to light. When other film types are covered on the ISFET, other kinds of ions can be detected.

U.S. Pat. No. 5,833,824 discloses an ISFET sensor for detecting ion activity in a solution, which includes a substrate and an ISFET semiconductor die. The substrate has a front surface exposed to the solution, a back surface opposite to the front surface and an aperture extending therebetween. A detecting film of the ISFET is mounted on the back surface such that the gate region is exposed to the solution through the aperture.

U.S. Pat. No. 4,691,167 discloses a method of measuring ion activation in a solution by combining the ISFET, the reference electrode, the temperature sensor, amplifier circuit and a calculation and memory circuit. Since the sensitivity is a function of the temperature and drain current of ISFET and is decided by a variable of gate voltage, the sensitivity can be obtained by calculating formulas stored in memory.

U.S. Pat. No. 5,130,265 discloses a method of fabricating the ISFET with multiple functions. The method uses siloxanic prepolymer as the sensitive film, mixing the solution, photochemistry treatment and heat treatment.

U.S. Pat. No. 4,660,063 discloses a method of performing both laser drilling and solid diffusion to form a 3D diode array on the semiconductor wafer. The laser first drills the wafer, and the impurities are then diffused from the hole to form a cylindrical PN junction and complete a non-planar ISFET structure.

U.S. Pat. No. 4,812,220 discloses an ISFET made by fixing the enzyme on the detecting film to measure the concentration of amino acids in food. The enzyme sensor is miniaturized, and can accurately measure concentrations, even when small.

There are many materials acting as detection membranes of ISFETs, such as, $Al_2O_3$, $Si_3N_4$, $Ta_2O_5$, a-$WO_3$, a-Si:H and the like. These thin films are deposited by either sputtering or plasma enhanced chemical vapor deposition (PECVD), therefore, the cost of the thin film fabrication is higher. For commercial purpose, it is important to develop a thin film, with low cost and easy fabrication.

In the ISFET applications, however, many factors such as hysteresis, temperature, and drift behavior affect the accuracy of the measuring results. Since pH-ISFET is a semiconductor device, it is easily influenced by variations in temperature. The variation of the temperature leads to a deviation of the measurement. With reference to the hysteresis behavior, it is related to the change in the pH of the solution (such as $pH_x \rightarrow pH_y \rightarrow pH_x \rightarrow pH_z \rightarrow pH_x$) and the corresponding change in the output voltage of the ISFET (such as $V_{ox1} \rightarrow V_{oy} \rightarrow V_{ox2} \rightarrow V_{oz} \rightarrow V_{ox3}$). At the same pH, the difference between the first output voltage and the final output voltage (such as $V_{ox3} - V_{ox1}$) is defined as the hysteresis width. For drift behavior, the drift rate is defined as the change in the gate voltage per unit time under conditions in which the source-drain current is stable and the temperature is constant after the intrinsic response of the pH-ISFET is completed. Hence, there is a need to measure the three effects to prevent error.

SUMMARY OF THE INVENTION

In view of this, an object of the invention is to provide a SnO₂ gate ISFET. The invention forms the SnO₂ layer as the detection membrane of the ISFET by sol-gel technology.

Another object of the invention is to provide a method of measuring temperature parameters of an ISFET. In the present invention, the sensitivities of the ISFET at different temperatures are obtained by the source-drain current and gate voltage of the ISFET in a solution, and temperature parameters (temperature coefficient of the sensitivity) of an ISFET are further obtained.

In the method of measuring the temperature parameters of an ISFET according to the present invention, the detecting film is immersed in a buffer solution, and, then, at a predetermined temperature, the pH of the buffer solution is changed to measure and record the source-drain current and the gate voltage of the ISFET to obtain a curve. The temperature parameters at the predetermined temperature are obtained by selecting a fixed current from the curve. The temperature parameters at other temperatures are obtained by changing the temperature of the buffer solution and the steps of measuring, recording and selecting.

Another object of the present invention is to provide a method of measuring the hysteresis width and drift rate of the $SnO_2$ ISFET to use the reverse compensation method to obtain the accurate output value.

In the method of measuring the hysteresis width of a $SnO_2$ ISFET according to the present invention, first, the drain-source current and then the drain-source voltage are fixed by a constant voltage/current circuit, and the $SnO_2$ ISFET is immersed in a buffer solution. The gate-source output voltage of the $SnO_2$ ISFET is recorded by a voltage-time recorder, and the pH of the buffer solution is changed. The steps of immersing and recording are then repeated to obtain the gate-source output voltages of the ISFET immersed in the buffer solution with different pH. The hysteresis width is the voltage deviation between starting pH and ending pH.

In the method of measuring the drift rate of a $SnO_2$ ISFET according to the present invention, first, the drain-source current and then the drain-source voltage are fixed by a constant voltage/current circuit, and the $SnO_2$ ISFET is immersed in a buffer solution. The gate/source output voltage of the $SnO_2$ ISFET during a constant period is recorded by a voltage recorder. The pH of the buffer solution is changed and the steps of immersing and recording are repeated to obtain the gate-source output voltages of the ISFET immersed in the buffer solution with different pH. The drift rate is the slope of the gate-source output voltage with respect to time.

Another object of the present invention is to provide an apparatus to measure the hysteresis width and the drift rate. The apparatus of measuring the hysteresis width and the drift rate has a $SnO_2$ ISFET, a buffer solution to contact the ISFET, a light-isolation container to load the buffer and to isolate light, a heater to heat the buffer solution, a constant current/voltage measuring device coupled to the source and drain of the $SnO_2$ ISFET, and a voltage-time recorder to record the output voltage of ISFET.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by way of illustration only, and thus are not limitative of the present invention, and wherein.

DETAILED DESCRIPTION OF THE INVENTION

Figure 1A:
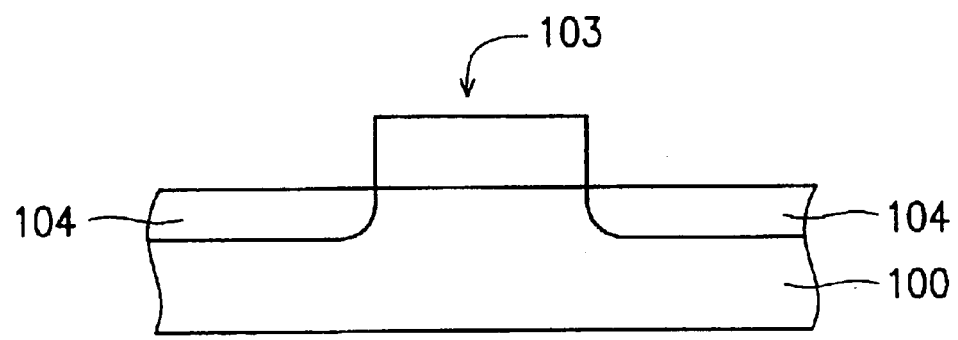
FIGS. 1a to 1c are cross-sections of the processes according to the present invention.
Figure 1B:
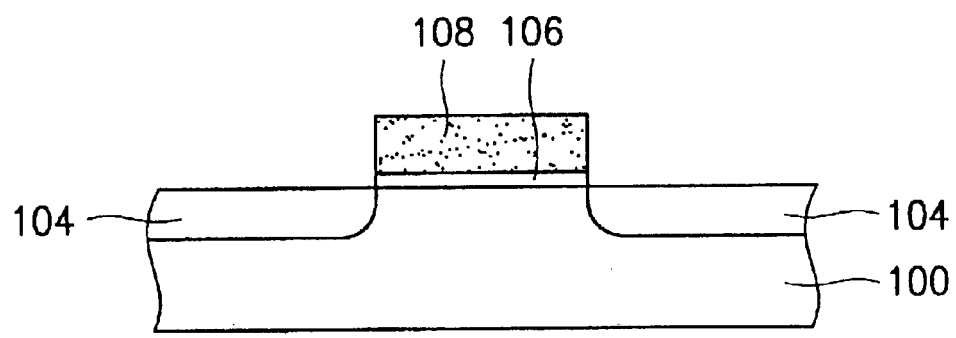
Figure 1C:
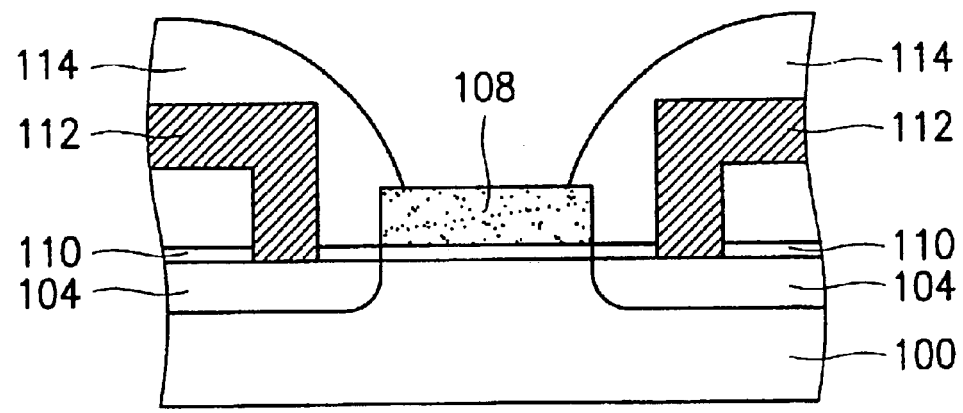

The $SnO_2$ gate ion sensitive field effect transistor ($SnO_2$ gate ISFET) according to the present invention is illustrated in FIGS. 1a to 1c.

As shown in FIG. 1a, a P-type (100) semiconductor substrate 100 with a resistivity ranging from 8 to 12 Ω-cm is provided. A pad oxide layer consisting of silicon dioxide with a thickness of 5000 Å is formed on the substrate 100 by wet oxidation. A first photoresist pattern (not shown) is formed on the pad oxide layer by conventional photolithography. A dummy gate 103 is formed to define the subsequent gate area, using the photoresist pattern as a mask to a portion of the pad oxide layer.

Impurities are then implanted into the semiconductor substrate 100 to form a source/drain 104 beside the dummy gate 103, using the dummy gate 103 as a mask. For example, the impurities implanted herein are boron ions with a dose of $10^{15}$ $cm^{-2}$.

As shown in FIG. 1b, the dummy gate 103 is removed, namely, the pad oxide layer 102 and the first photoresist pattern are removed by wet etching. An insulating layer 106 consisting of silicon dioxide with a thickness of about 1000 Å is then formed on the semiconductor substrate 100. A second photoresist pattern (not shown) is formed on the insulating layer 106 by photolithography. Next, the insulating layer 106 outside the gate area is removed by the second photoresist pattern as a mask. The residual insulating layer within the gate area is used as a gate oxide layer. Subsequently, the second photoresist layer is removed.

A $SnO_2$ layer 108 is then formed on the insulating layer 106 by sol-gel technology. For example, the $SnO_2$ layer 108 with a thickness of least 1000 Å is formed on the insulating layer 106. A two-layer gate consisting of the gate oxide layer 106 and the $SnO_2$ layer 108 is fabricated. Thus, a $SnO_2$ ISFET is obtained. The $SnO_2$ ISFET has a channel length of about 50 µm and a channel width of about 1000 µm. Thus, the aspect ratio (channel width/channel length) of the present $SnO_2$ ISFET is 20.

Next, as shown in FIG. 1c, an interconnecting process is performed to obtain the ion sensitive field effect transistor (ISFET) using conventional interconnect steps for MOS. Thus, an insulating layer 100 is formed on the source/drain 104, and a metal wire 112 is formed on the insulating 110 by etching and sputtering. Finally, a sealing layer 114 consisting of the insulator is formed to seal the metal wire excluding the $SnO_2$ layer 108. For example, the metal wires 112 can be aluminum, and the sealing layer 114 can be epoxy resin.

The step of forming the $SnO_2$ layer 108 on the gate oxide layer 106 by sol-gel technology is illustrated as follows.

First, a mixing solution consisting of $SnCl_2 \cdot 2H_2O$ and ethanol is prepared at a concentration of about 0.37M. The mixing solution is then coated on the surface of the gate oxide layer 106 of the ISFET. Finally, the ISFET coated with mixing solution is heated at a temperature of about 350° C. to 400° C. for one hour. After that, the $SnO_2$ gate layer 108 is obtained on the oxide layer 106 for the $SnO_2$ ISFET.

The use of sol-gel technology to form the $SnO_2$ detection membrane provides a low temperature process using less equipment at a lower cost, and enables formation of a thin, uniform detection membrane. Additional benefits also include easily formed $SnO_2$ detection membrane on a large area surface of the substrate, easy modification of the components of the sol-gel to produce the desired detection membrane, and more easily controlled accuracy in microstructure of the detection membrane, such as porosity, aperture, and specific surface.

Figure 2:
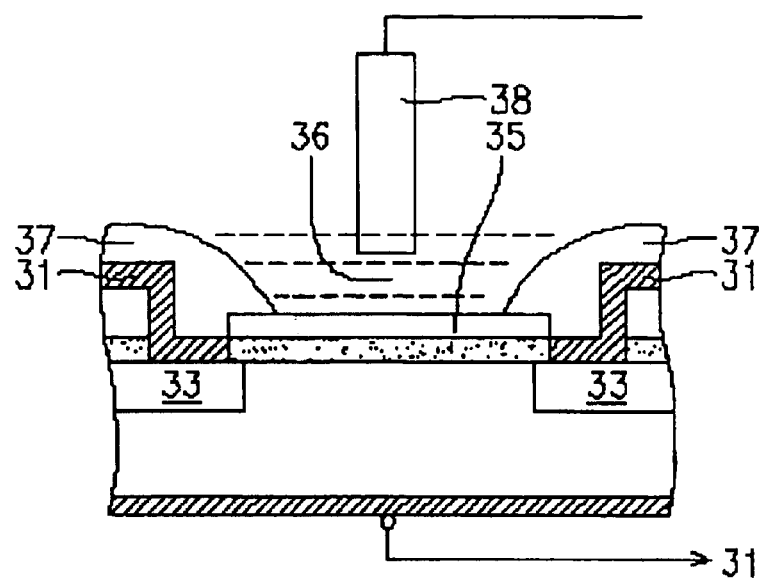
FIG. 2 is a cross-section of an ISFET with gate consisting of $SnO_2$.

FIG. 2 is a cross-section of the $SnO_2$ ISFET according to the present invention. The structure of this ISFET is similar to that of MOSFET. The difference between the ISFET and MOSFET is that the metal gate of the MOSFET is replaced by a $SnO_2$ detection membrane 35, an aqueous solution 36 and reference electrode 38. The circuits are formed by contacting the metal wire 31, preferably consisting of Al, with the source/drain 33. Since the $SnO_2$ detection membrane 35 contacts the detected solution 36, the whole device in addition to the $SnO_2$ detection membrane 35 must be enclosed by a sealing layer 37 consisting of a material with good insulating property, such as epoxy resin. The reference electrode 38 provides a detecting base.

The $SnO_2$ detection membrane 35 of the ISFET is immersed in the solution 36 during operation, such that the point of transformation from chemical equivalence into electrical equivalence within the ISFET occurs with contact between the $SnO_2$ detection membrane 35 and the aqueous solution 36. The reaction mechanism of the ionic activity within the solution is the interface potential obtained from the interface between the aqueous solution 36 and the $SnO_2$ detection membrane 35 immersed in the aqueous solution 36. The interface potential varies with the ionic activities of various aqueous solutions. In addition, the interface potential regulates the channel conduction of the ISFET and results in the change of current within the source/drain 33.

Figure 3:
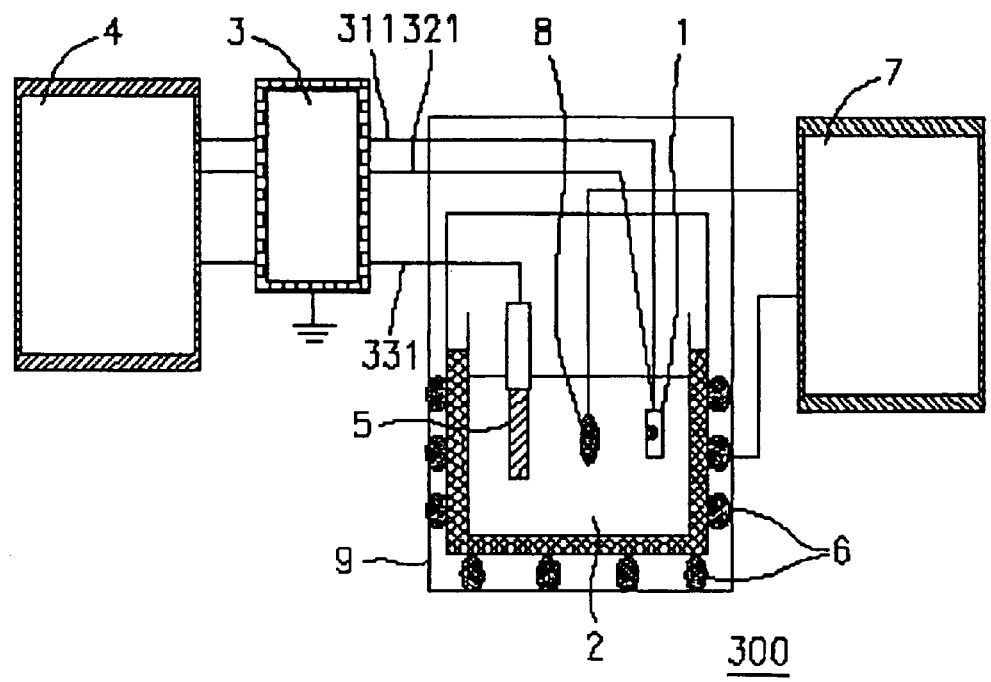
FIG. 3 is a schematic structural diagram of the apparatus to measure the temperature parameter of the $SnO_2$ ISFET according to the present invention.

FIG. 3 shows a systematic structure diagram according to the invention. An ISFET using $SnO_2$ as a detection membrane (called $SnO_2$ ISFET) is immersed in a buffer solution 2 such as the phosphate buffer solution that is stored in a container (not titled). The source/drain (not shown) of the $SnO_2$ ISFET 1 connects a test fixer 3 through two connecting wires 331, respectively, to convey the electrical signal obtained by measuring the source/drain to a current/voltage measuring device 4, such as the Keithley-236 current/voltage measuring device for data processing.

Also, a reference electrode 5 is disposed in the buffer solution 2, with one end connected to the test fixer 3 through the connecting wire 331. A plurality of heater 6 is disposed outside the container and connected to a PID temperature controller 7. A thermometer 8 connected to the PID temperature controller 7 detects the temperature of the buffer solution 2. The above-mentioned elements such as the buffer solution 2, the elements contacting the buffer solution 2 and the heater 6 are placed in a light-isolating container 9 to prevent the measuring data from the effect of light.

It should be noted that the interfacial potential between the $SnO_2$ membrane and the solution, and the characteristic difference of charge density in the reverse layer of the semiconductor surface is used to measure needed data (such as the source-drain current or the gate voltage) and thus obtain the temperature parameters of the ISFET.

Figure 4:
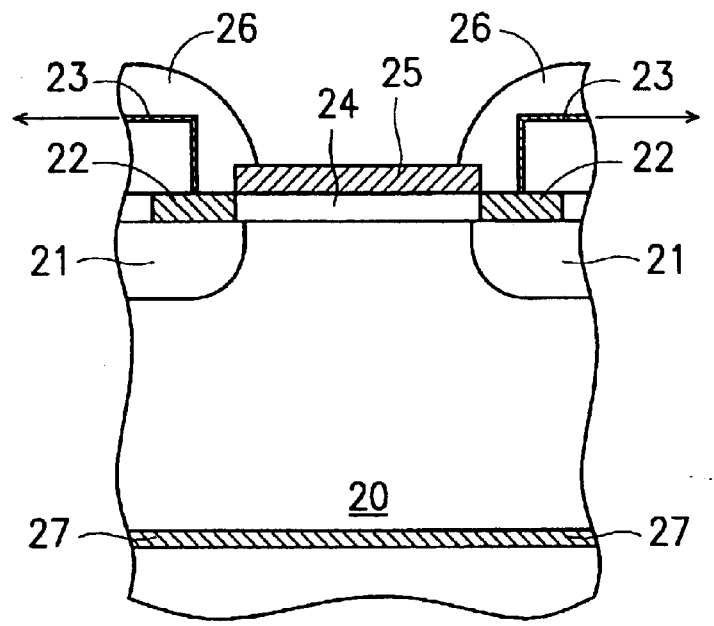
FIG. 4 is a schematic cross-section of the $SnO_2$ ISFET according to the present invention.

FIG. 4 is a schematic cross-section of the $SnO_2$ ISFET according to the present invention. The $SnO_2$ ISFET is formed on a semiconductor substrate 20 such as a p-type silicon substrate. A pair of source/drain regions 21 separated from each other are formed approaching the top surface of the semiconductor substrate 20 and each region 21 is connected to the test fixer outside through an aluminum contact plug 22 and an aluminum wire 23. On the semiconductor substrate 20 between the two drain/source regions 21, a gate oxide 24, like a silicon oxide layer, and a $SnO_2$ detection membrane 25 are formed sequentially. An epoxy resin 26 seals the device but exposes the $SnO_2$ detection membrane 25. As well, a metal-aluminum layer 27 is formed at the bottom of the semiconductor substrate 20 to shield light and decrease its influence on charge carriers.

Figure 5:
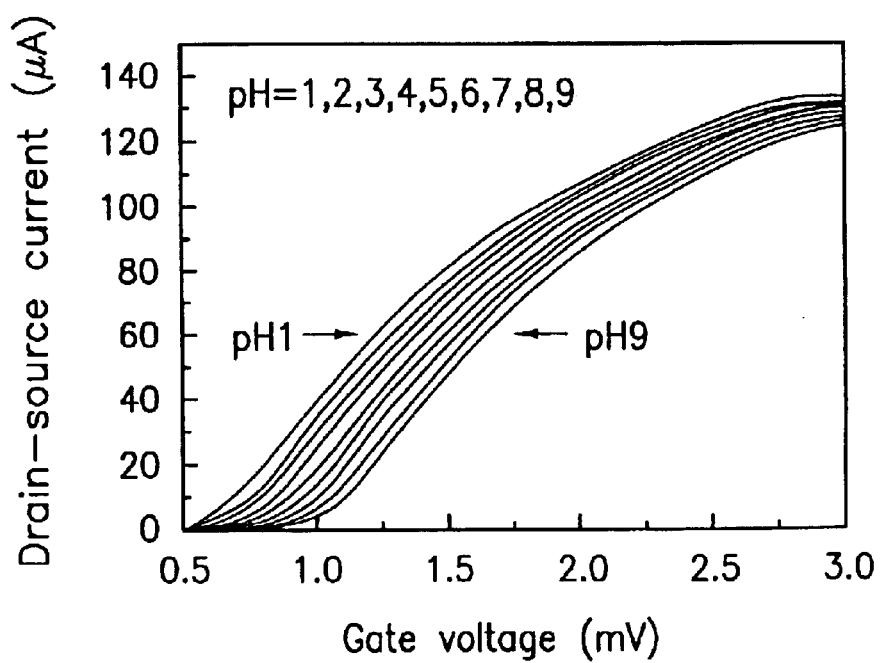
FIG. 5 shows a curve related to the source/drain current and the gate voltage of the $SnO_2$ ISFET at 25° C. according to the present invention.

With reference to apparatus shown in FIG. 3 and FIG. 4, the temperature parameters of the $SnO_2$ ISFET of the present invention can be obtained according to a method as follows. First, with regard to the measurement of the sensitivity, the detection membrane of the $SnO_2$ ISFET contacts with the buffer solution. The temperature of the buffer solution is fixed, such as at 25° C., and the pH of the buffer solution is changed at the same time. The curve related to the source-drain current and the gate voltage of the $SnO_2$ ISFET is measured and recorded by the Keithley-236 current/voltage measuring device. FIG. 5 shows curves related to the statistical result, and both the source-drain current and the gate voltage of the $SnO_2$ ISFET rise as the pH of the buffer resolution increases.

Figure 6:
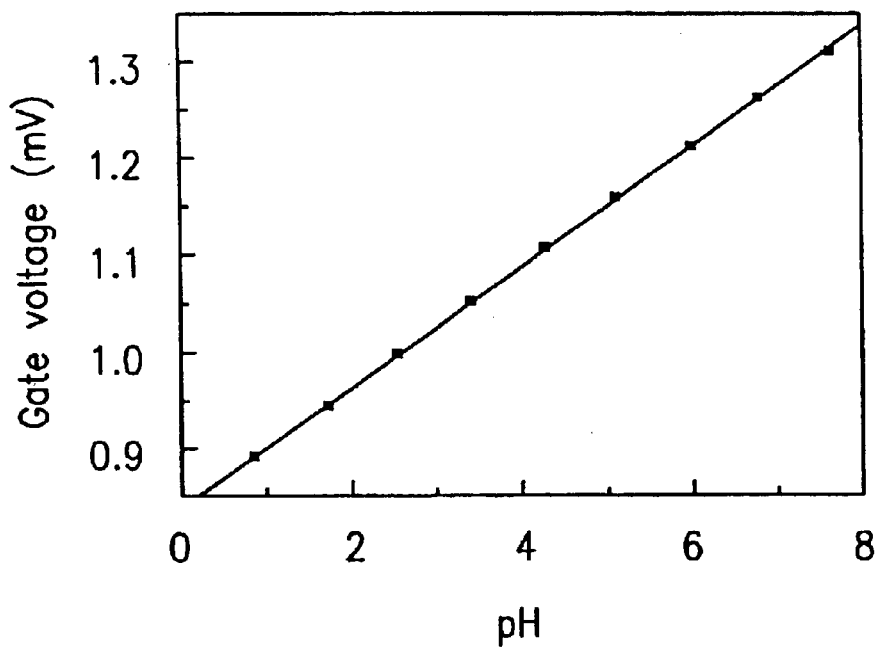
FIG. 6 shows a curve related to the gate voltage of the $SnO_2$ ISFET and the pH.

Next, a fixed current of the curve (like 80 $\mu$A) is selected to obtain a curve related to the gate voltage and the pH at a specific temperature (like 25° C.) as shown in FIG. 6, wherein the sensitivity of the $SnO_2$ ISFET at 25° C. is 57.36 mV/pH. It is found that the gate voltage of the $SnO_2$ ISFET is in direct proportion to the pH of the buffer solution and the slope of the curve is the sensitivity of the $SnO_2$ ISFET at the specific temperature.

Moreover, in order to measure the sensitivity of the $SnO_2$ ISFET at different temperatures, only the temperature of the buffer solution needs to be changed, such as between 15° C.~45° C., with the above step repeated at each temperature. Table 1 shows the sensitivity of the ISFET at the different temperatures.

TABLE 1

| the sensitivity of the ISFET at the different temperatures | | | | |
| --- | --- | --- | --- | --- |
| Temperature (° C.) | 15 | 25 | 35 | 45 |
| Sensitivity (mV/pH) | 55.1 | 57.16 | 58.66 | 60.36 |

Figure 7:
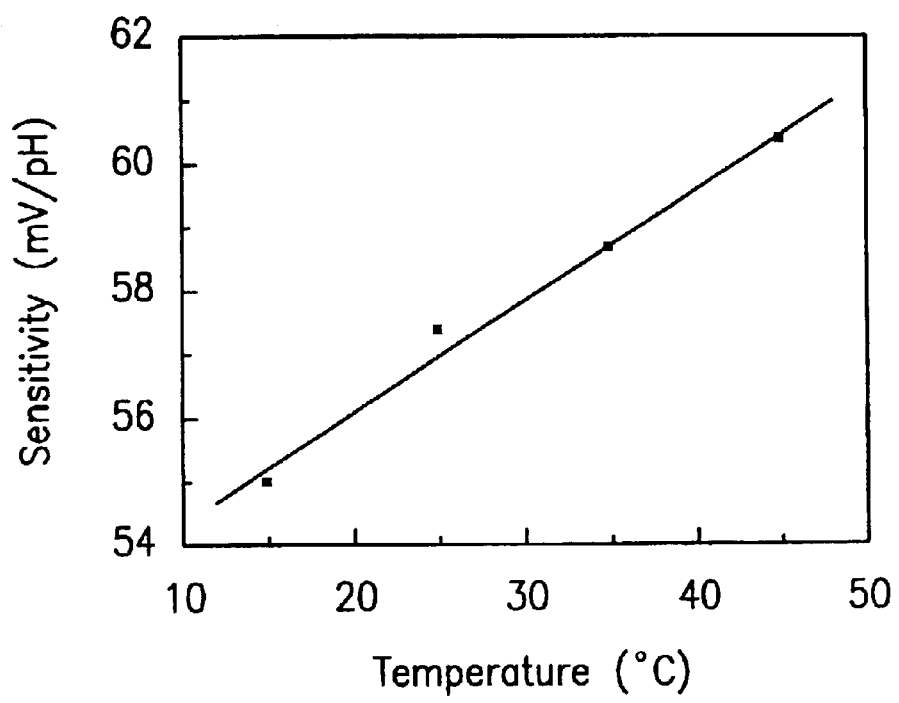
FIG. 7 shows a curve related to the sensitivities of the $SnO_2$ ISFET and the temperature according to the present invention.

A curve showing the obtained sensitivities at different temperatures is shown in FIG. 7, wherein the sensitivity is in direct proportion to the rising temperature and the slope of the curve is about 0.173 mV/pH° C. Namely, the temperature parameter of the $SnO_2$ ISFET is about 0.173 mV/pH° C.

Figure 8:
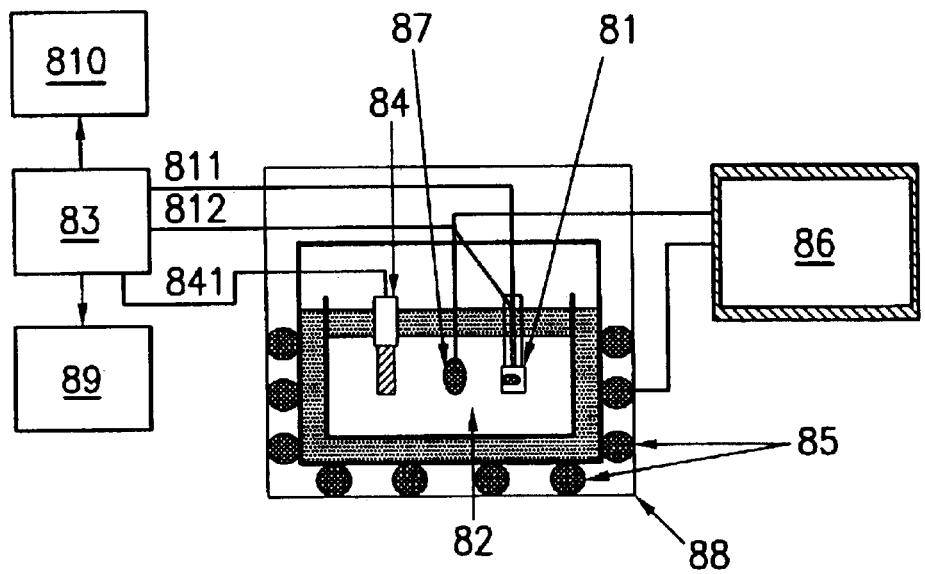
FIG. 8 shows a schematic structure diagram of the apparatus to measure the hysteresis width and drift rate of the $SnO_2$ ISFET according to the present invention.

FIG. 8 shows a schematic diagram to measure the hysteresis width and the drift rate of an ISFET with $SnO_2$ as a detection membrane according to present invention. An ISFET 81 with $SnO_2$ as a detection membrane (called $SnO_2$ ISFET) is immersed in a buffer solution 82 such as a standard buffer solution and carried by a container (not labeled). A drain/source (not shown) of the $SnO_2$ ISFET 81 is connected to a constant voltage/current circuit 83 (such as a negative feedback circuit) through two wires 811 and 812. The drain-source voltage and the drain-source current of the $SnO_2$ ISFET 81 are fixed by the constant voltage/current circuit 83.

A reference electrode 84 is disposed in the buffer solution 82, wherein one end of the reference electrode 84 is connected to the constant voltage/current circuit 83 through a wire 841. A heater 85 disposed outside the container is connected to a PID (Proportional-Integral-Derivative) temperature controller 86. Both the heater 85 and the PID temperature controller 86 keep the buffer solution 82 at a constant temperature (preferably 25° C.) detected by a thermocouple 87 connected to the PID temperature controller 86. The above buffer solution 82, every device connected thereto, and the heater 86 are disposed in a light-isolating container 88 to reduce the effect of light on the measuring results.

The constant voltage/current circuit 83 is connected to a current/voltage measuring device 89 composed of two digital multimeters detecting whether the source-drain current and the source-drain voltage of the $SnO_2$ ISFET 81 move towards stability. Also, the constant voltage/current circuit 83 is connected to a voltage-time recorder 810 for setting and recording the output voltages during each recording period.

Figure 9:
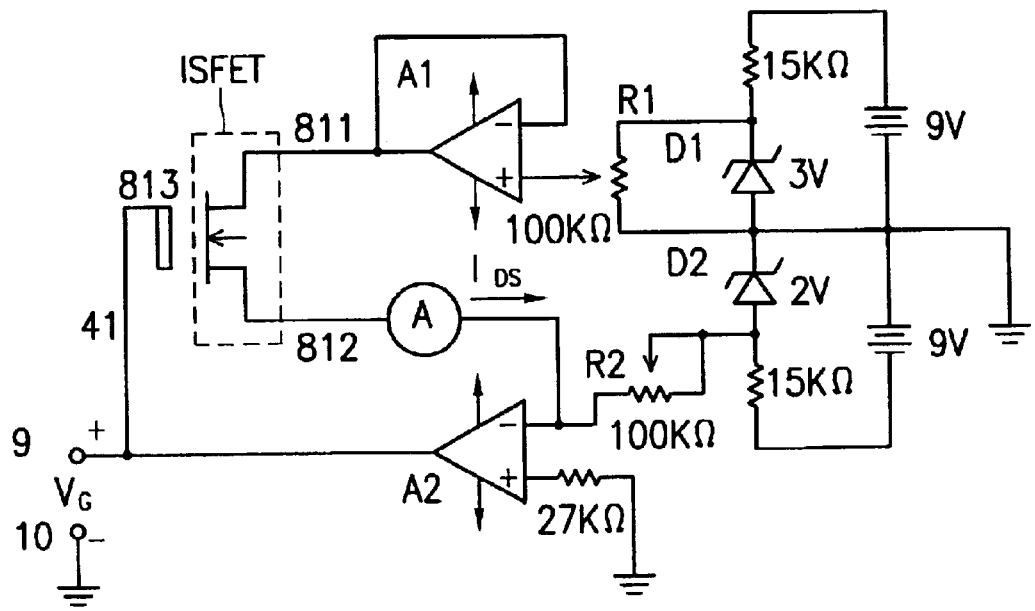
FIG. 9 shows a schematic diagram of the constant voltage current circuit according to the present invention.

FIG. 9 shows a schematic diagram of the constant voltage/current circuit 83 according to the present invention. The constant voltage/current circuit 83 is connected to the source/drain of the $SnO_2$ ISFET 81 through the wires 811 and 812, and is connected to the reference electrode 84 through the wire 841. The source-drain voltage is fixed at a constant value (preferably 0.2V) by adjusting the variable resistance R1. The source-drain current is fixed at a constant value (preferably 50 $\mu$A). In this case of the negative feedback circuit, the output voltage and the gate voltage are reduced and finally the drain-source current $I_{DS}$ is reduced when the increasing drain-source current $I_{DS}$ increases the source voltage. The circuit 83 has advantages of simplicity, low cost, ease of operation and no need for adjustment of the measuring point.

Next, returning to FIG. 4, a schematic cross-section of the $SnO_2$ ISFET according to the present invention, the $SnO_2$ ISFET is formed on a semiconductor substrate 20 such as a p-type silicon substrate. In this case, a pair of source/drain regions 21 separated from each other are formed approaching the top surface of the semiconductor substrate 20, and are connected to constant voltage/current circuit by an aluminum contact plug 22 and an aluminum wire 23. On the semiconductor substrate 20 between the two drain/source regions 21, a gate oxide 24, such as a silicon oxide layer, and a $SnO_2$ detection membrane 25 are formed sequentially. An epoxy resin 26 seals the device but exposes the $SnO_2$ detection membrane 25. As well, a metal-aluminum layer 27 is formed at the bottom of the semiconductor substrate 20 to decrease the channel-adjusting effect.

Hereinafter, a method to measure the hysteresis width and the drift rate of the $SnO_2$ ISFET in detail is described with reference to FIGS. 2, 8 and 9.

With reference to the method of measuring the hysteresis width of the $SnO_2$ ISFET, first, the drain-source current and the drain-source voltage of the $SnO_2$ ISFET 81 are fixed by the constant voltage/current circuit (negative feedback circuit) 83. In this step, the $SnO_2$ ISFET and the reference electrode are connected to the constant voltage/current circuit 83, and are immersed in the solution. Next, the drain voltage $V_D$ of the $SnO_2$ ISFET 81 is set at 0.2V by adjusting the variable resistant R1 and measuring by one digital multimeter. Also, the drain-source current $I_{DS}$ is set at 50 $\mu$A by adjusting the variable resistant R2 and measuring by the other digital multimeter. The $SnO_2$ ISFET 81 is then placed in a standard solution to maintain stability.

After, the $SnO_2$ ISFET 81 is immersed in a buffer solution. Next, the voltage-time recorder records the gate-source output voltages of $SnO_2$ ISFET 81. The hysteresis width of the $SnO_2$ ISFET in accordance with the pH of the buffer solution is then measured. In the present invention, hysteresis width is measured in pH=5→1→5→9→5 order, namely pH=5-4-3-2-1-2-3-4-5-6-7-8-9-8-7-6-5, wherein each measuring result is achieved at the time the pH is changed for one minute, the loop time is 1020 seconds, and one time the pH changes one unit. Particularly, choosing the pH=5-1-5-9-5 order measures hysteresis within the pH range between 1 and 9. Also, the hystereses within the pH range between 1 and 9 are measured in the same way, wherein each result is at the time when the pH is changed for two minutes and four minutes, the loop time is 2040 seconds and 4080 seconds. Table 2 shows the hysteresis width of the $SnO_2$ ISFET in pH=5→1→5→9→5 order at different loop time. By the same method, all of the hysteresis width at different pH values can be measured, helpful in performing the reverse compensation method. Table 3 shows the hysteresis width of the $SnO_2$ ISFET in pH=4→1→4→7→4 order at different loop time.

TABLE 2

| the hysteresis width of the $SnO_2$ ISFET in pH = 5→1→5→9→5 order at different loop time | |
|---|---|
| Loop time (seconds) | Hysteresis width (mV) |
| 1020 | 3.74 |
| 2040 | 4.79 |
| 4080 | 5.46 |

TABLE 3

| the hysteresis width of the $SnO_2$ ISFET in pH = 4→1→4→7→4 order at different loop time | |
|---|---|
| Loop time (seconds) | Hysteresis width (mV) |
| 980 | 1.3 |
| 1960 | 2.85 |
| 3920 | 4.47 |

Figure 10:
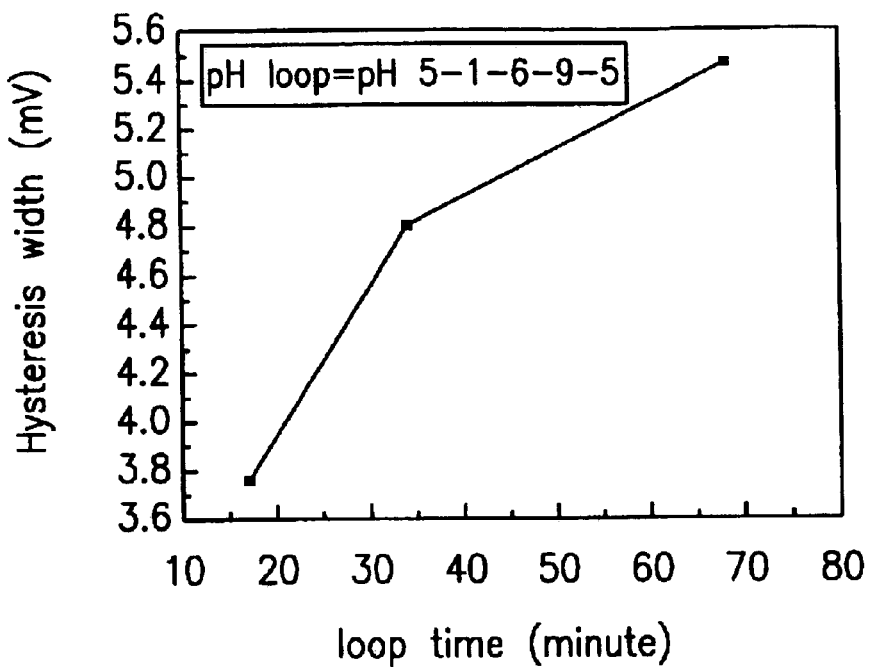
FIG. 10 shows the relationship between the hysteresis width and time in pH=5→1→5→9→5 order.
Figure 11:
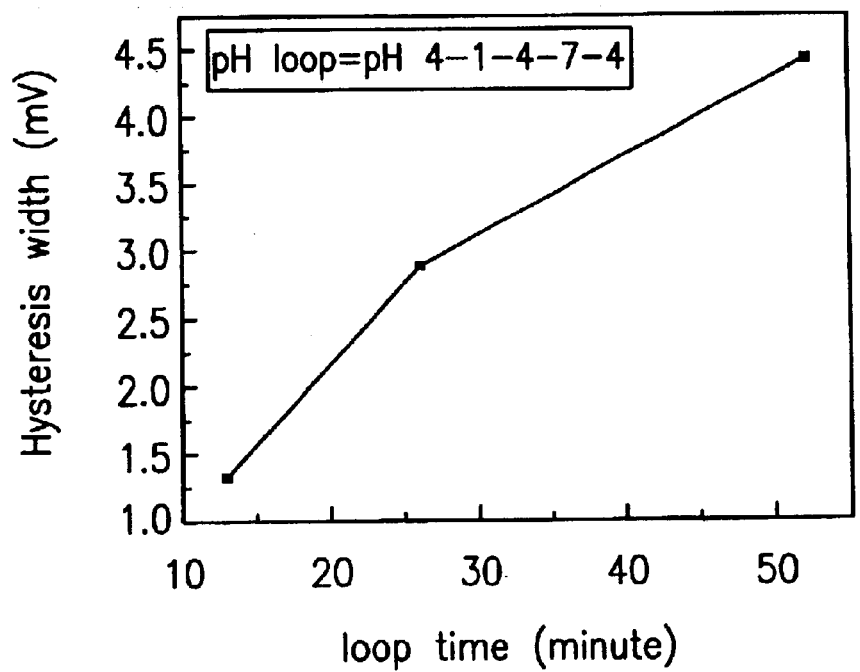
FIG. 11 shows the relationship between the hysteresis width and time in pH=4→1→4→7→4 order.

The relationship between the hysteresis width, the pH and time measured in pH=5→1→5→9→5 order is shown in FIG. 10. Also the relationships of the hysteresis width, the pH and time measured at pH=4→1→4→7→4 order is shown in FIG. 11. As shown in FIGS. 10 and 11, the hysteresis width of the $SnO_2$ ISFET increases as the loop time increases.

Next, with reference to the drift rate, the drain-source current and the drain-source voltage of the $SnO_2$ ISFET is fixed by the constant voltage/current circuit (negative feedback circuit) 83. The $SnO_2$ ISFET and the reference electrode are then connected to the constant voltage/current circuit 83, and immersed in the solution. Next, the drain-source current $I_{DS}$ of the ISFET is set by adjusting the variable resistor R2 and measurement by one digital multimeter. Also, the drain-source voltage $V_{DS}$ is set at 0.2V by adjusting the variable resistor R1 and measuring with the other digital multimeter. Afterwards, the $SnO_2$ ISFET is immersed in the buffer solution for a period of time. Finally, the gate-source output voltage is recorded by the voltage-time recorder, thereby obtaining the drift rate of the ISFET.

It should be noted that current generated by illumination affects the drift rate. Hence, the drain-source current should be adjusted between 10 $\mu$A and more than one hundred $\mu$A to reduce the illumination effect. As well, stability is easily affected by temperature when the drain-source current $I_{DS}$ is extremely large. Accordingly, the drain-source current is preferably set at 10~300 $\mu$A.

Figure 12:
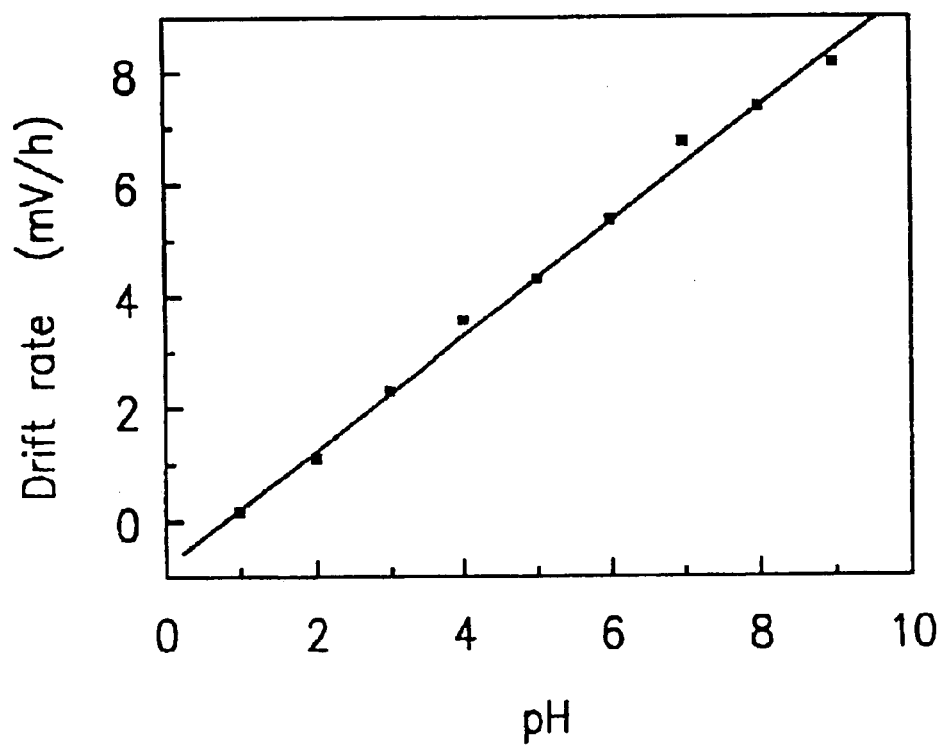
FIG. 12 shows the relationship between the drift rate of the $SnO_2$ and the pH.

Table 4 shows the drift rates of the $SnO_2$ ISFET at pH 1~9, and FIG. 12 shows the relationship between the drift rate and the pH. The drift rate of the $SnO_2$ ISFET is obtained from the slope of the curve whose time parameter is more than the fifth hour.

TABLE 4 the drift rates of the SnO₂ ISFET at pH 1~9

| pH | Drift rate (mV/h) |
|---|---|
| 1 | 0.11 |
| 2 | 1.07 |
| 3 | 2.28 |
| 4 | 3.52 |
| 5 | 4.28 |
| 6 | 5.35 |
| 7 | 6.73 |
| 8 | 7.37 |
| 9 | 8.15 |

It is believed that the drift behavior is more obvious when the pH is large. Also, when the data approximately form a line, the drift rates at any other pH can be estimated. This is useful when performing reverse compensation.

The method of forming the $SnO_2$ ISFET according to the present invention is simple, has a low cost and novel technology. The measuring methods and apparatus can accurately measure hysteresis width and drift rate of the $SnO_2$ ISFET, and also hysteresis width and the drift rate of the ISFETs with other types of detection membranes.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation to encompass all such modifications and similar arrangements.

What is claimed is:

1. A method of measuring the temperature parameters, comprising:
    contacting a $SnO_2$ detection membrane of an ISFET with a buffer solution;
    changing the pH of the buffer solution at a predetermined temperature;
    measuring and recording the source-drain current and the gate voltage of the ISFET to obtain a curve, wherein an interfacial potential between the $SnO_2$ detection membrane and the buffer solution being used to measure the source-drain current or the gate voltage;
    selecting a fixed current from the curve to obtain the sensitivity of the ISFET at the predetermined temperature;
    changing the temperature of the buffer solution and repeating the steps of contacting, changing the pH, measuring, recording and selecting to obtain the sensitivities of the ISFET at different temperatures.

2. The method as claimed in claim 1, wherein the increment of the gate voltage is caused by increasing per unit pH at the predetermined temperature.

3. The method as claimed in claim 2, wherein the predetermined temperature is fixed by a temperature controller and a heater.

4. The method as claimed in claim 3, wherein the predetermined temperature is between 15° C. and 45° C.

5. The method as claimed in claim 4, wherein the pH of buffer solution is between 1 and 10.

6. A method of measuring the hysteresis width, comprising the steps of:
    fixing the drain-source current and the drain-source voltage of an ISFET with a $SnO_2$ detection membrane by a constant voltage/current circuit;
    contacting the detection membrane in a buffer solution;
    recording the gate/source output voltage of the ISFET by a voltage-time recorder; and
    changing the pH of the buffer solution and repeating the step of fixing, immersing and recording to measure the hysteresis width of the ISFET.

7. The method as claimed in claim 6, wherein the hysteresis width is the change in the gate/source output voltage from the first measuring point to the final measuring point.

8. The method as claimed in claim 6, wherein the source-drain current is fixed at 50 $\mu$A, and the drain-source voltage is fixed at 0.2V.

9. The method as claimed in claim 6, further comprising immersing the ISFET with the $SnO_2$ detection membrane in a standard solution to maintain stability prior to immersing the $SnO_2$ detection membrane into the buffer solution.

10. The method as claimed in claim 6, wherein the pH is changed from pH=4 to pH=1, to pH=4, to pH=7, and to pH=4.

11. The method as claimed in claim 10, wherein each pH level of the buffer solution is fixed for one minute.

12. A method of measuring the drift rate comprising:
    fixing the drain/source current and the drain/source voltage of an ISFET with a $SnO_2$ detection membrane by a constant voltage/source circuit;
    contacting the $SnO_2$ detection membrane into a buffer solution;
    recording the gate/source output voltage of the $SnO_2$ ISFET during constant period by a voltage-time recorder to obtain the drift rate of the $SnO_2$ ISFET.

13. The method as claimed in claim 12, further comprising a step of changing the pH of the buffer solution to measure the drift rates of the $SnO_2$ ISFET at different pH levels.

14. The method as claimed in claim 13, wherein the drift rate is the change in the gate/source voltage per unit of time.

15. The method as claimed in claim 13, wherein the gate/source current is fixed at 50 $\mu$A, and the drain-source voltage is fixed at 0.2V.

16. The method as claimed in claim 12, further comprising a step of immersing the $SnO_2$ ISFET in a standard solution to maintain stability prior to immersing the $SnO_2$ ISFET in the buffer solution.

17. The method as claimed in claim 14, wherein the gate/source output voltage of the $SnO_2$ ISFET is recorded for more than twelve hours.

* * * * *